(12) United States Patent
Wilson, Jr. et al.

(10) Patent No.: US 9,061,229 B1
(45) Date of Patent: *Jun. 23, 2015

(54) DETECTOR FOR CLOGGED FILTERS

(71) Applicant: Filtersmarts, Inc., Huntsville, AL (US)

(72) Inventors: David J. Wilson, Jr., Huntsville, AL (US); Douglas Morris, Madison County, AL (US)

(73) Assignee: Filtersmarts, Inc., Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/290,025

(22) Filed: May 29, 2014

Related U.S. Application Data

(63) Continuation of application No. 13/457,952, filed on Apr. 27, 2012, now Pat. No. 8,744,780.

(51) Int. Cl.
G01N 21/01 (2006.01)
B01D 46/00 (2006.01)
G01N 21/59 (2006.01)

(52) U.S. Cl.
CPC ............ B01D 46/0086 (2013.01); G01N 21/59 (2013.01); *G01N 2201/06* (2013.01)

(58) Field of Classification Search
CPC ............ G01N 21/35; G01N 2015/084; G01N 2015/0846

USPC ........................................................ 702/34, 35
See application file for complete search history.

(56) References Cited

U.S. PATENT DOCUMENTS

| | | | | |
|---|---|---|---|---|
| 5,679,137 A * | 10/1997 | Erdman et al. | ..................... | 96/26 |
| 7,012,685 B1 * | 3/2006 | Wilson | ..................... | 356/239.1 |
| 2005/0200474 A1 * | 9/2005 | Behnke | ..................... | 340/521 |
| 2008/0100826 A1 * | 5/2008 | Sharpe | ..................... | 356/51 |
| 2008/0314271 A1 * | 12/2008 | Goldfarb | ..................... | 101/401.1 |
| 2010/0313748 A1 * | 12/2010 | Schluter | ..................... | 95/25 |

* cited by examiner

*Primary Examiner* — Janet Suglo
*Assistant Examiner* — Michael Dalbo
(74) *Attorney, Agent, or Firm* — Stephen H. Hall; Jeremy A. Smith; Bradley Arant Boult Cummings LLP

(57) ABSTRACT

A clogged filter detector has a transmitter and a sensor which are held in place by a transmitter bracket and a sensor bracket, respectively. The transmitter emits a beam of electromagnetic radiation, and the sensor is positioned in the path of this beam at a point such that the beam travels through a filter between the transmitter and the sensor. The transmitter and sensor are mis-aligned with the air flow at the point where the beam contacts the filter. The transmitter alternates between a transmitting mode and a dormant mode, and the transmitter emits a plurality of electromagnetic pulses during each transmitting mode.

18 Claims, 6 Drawing Sheets

DETECTOR FOR CLOGGED FILTERS

A. CROSS REFERENCE TO OTHER APPLICATIONS

This application is a continuation of and therefore claims priority to, and the benefit of, currently pending U.S. patent application Ser. No. 13/457,952 filed Apr. 27, 2012, titled "Detector for Clogged Filters."

B. FIELD OF THE INVENTION

The present invention relates to detectors for determining when air filters have become clogged.

C. BACKGROUND AND DESCRIPTION OF THE RELATED ART

Filters for heating, ventilation, and air conditioning (HVAC) systems play an important role by minimizing deposits of dust and other particles on cooling coils and heating surfaces. Deposits of dust or other materials on cooling coils and heating surfaces reduce the efficiency, and therefore increase the energy needed to operate the HVAC system. A clogged filter can result in decreased air flow over cooling coils and heating surfaces, and decreased air flow also lowers efficiency and can shorten the life of a HVAC system because the HVAC system has to run longer to maintain the desired temperature.

After a period of use, dust accumulates on the filters, causing them to become clogged and requiring additional energy consumption. At some point, it becomes cost-effective to remove the filter and either clean it or replace it with a new one. HVAC equipment manufacturers typically state their warranties so that the user, not the manufacturer, is responsible for equipment failures due to neglect in maintaining the system. Manufacturers typically emphasis maintenance of the dust filters. In most cases, the manufacture does not have access to an operating HVAC system unless called by the user, so it is not practical for a manufacturer to be responsible for filter maintenance. It often takes weeks or months before an air filter needs to be cleaned or replaced, and the long periods of time and lack of constant attention can result in users neglecting air filter maintenance.

Many newer, high efficiency air-conditioners and heat pumps now use variable speed fan motors (ECM—Electronically Commutated Motors) which attempt to achieve constant, optimized flow through the dust filter and AC or heat pump coils, even as dust gradually clogs the filter. The filter can, never-the-less, eventually clog sufficiently that the air flow decreases. The increased fan motor power required to draw air through the clogging filter decreases the HVAC efficiency. Decreasing flow across the coils below the optimum flow rate also decreases the system efficiency. Increases in run time due to the clogged filter can both 1) increase energy requirements (decrease efficiency) and 2) decrease system lifetime, because HVAC system lifetime approximates inverse proportionality to system run-time.

In recent years, the lower costs and increased accuracies of differential pressure switches have led to their more frequent application for monitoring the clogging of dust filters. These instruments monitor differential pressure between the input and output sides of the filter. When the differential pressure reaches a predetermined level, an alarm is triggered which indicates the filter is clogged. Problems can occur from opening/closing of doors between rooms or other actions modifying ambient room pressure. Any ducting leaks, quite normal in older systems, also leads to increased flow of non-filtered (filter bypass) air as the filter becomes clogged. With increase dust loading and clogging of the dust filter, the filter will often physically warp so that air flows around the filter; i.e., a filter bypass air-flow path is created until the filter is cleaned or replaced.

An electro-optical dust filter sensor/alarm offers advantages over the differential pressure sensor in that it is not affected by the flow across the filter or by the speed of the HVAC fan motor. Since the invention of dust filters, the "eyeball" (visually examining the dust/dirt build-up on the filter's leading edge) has been the traditional means of determining when the filter needs replacing or cleaning. This eyeball examination is often left to the memory of the user, which may be aided by such things as a calendar date (i.e., the first of each month).

Some electro-optical based clogged dust filter detectors are designed for use with low optical density filter media. However, a filter detector which functions with filters designed for smaller (sub-micron) particle removal is desirable. These filters are necessarily more optically dense than traditional low optical density filter media, and therefore require an optical filter detector that has increased optical sensitivity.

One example of an optical filter detector comprises a simple light emitting diode (LED) coupled to a receiving photo-diode (or photo-transistor) with a simple signal processor. This filter detector may perform the required task with the lower cost, lower optical density, lower MERV (minimum efficiency reporting value) rated dust filters. However, as the filters become more optically dense to remove smaller (few micron to submicron) particles (i.e., filters with higher MERV values), the simple optical transmitter/sensor electro-optical filter detectors are not sufficient.

The cheaper, lower MERV filters typically either have no pleats or pleats with a spacing of 1 to 2 pleats (folds) per inch; at least some of the high MERV filters are manufactured with a pleat spacing of up to 8 pleats per inch. Thus the high MERV filters are more optically dense, especially when viewing across the pleats. Therefore the basic electro-optical system described above may not be suitable with the high MERV, optically dense filters such as the 3M® Filtrete® 1500, 1700 or 1900 brand or equivalent DuPont® filters. As stated above, high MERV filters remove a greater percentage of small (micron and submicron) particles than the cheaper filters. This is especially important for people with allergies or in clean room or sterile hospital situations requiring "clean air".

In order to operate with higher MERV, high efficiency (from small particle collection standpoint) filters, the filter detector must thus have adequate sensitivity to function with optically dense filter media. Also, since HVAC dust filters are often located in hallways with no available electrical power, a long-life, battery-powered filter detector can be desirable.

Filters can be used for a wide variety of purposes other than the HVAC systems discussed above. For example, filters are used to control incoming dust and outgoing paint particles for paint spraying operations. They are also used to control dust accumulation on electronic components for ventilated electronics enclosures such as those used by cable television companies on the side of the street. The clean environment used in fabrication of micro-electronic chips typically requires a filtered air source. Very clean (filtered) air is also required for some medical applications. These filter uses can all be referred to as HVAC (heating, ventilation and air-conditioning) applications.

Since the filter maintenance requirement is environment driven rather than time driven, a clogged filter sensor is helpful in maintaining HVAC system optimal operating efficiency. A system that notified the user when an air filter needed attention could minimize energy losses and decreased performance resulting from clogged air filters.

SUMMARY OF THE INVENTION

The present invention is directed to clogged filter detection systems. These systems generally comprise an optical transmitter adapted to transmit a beam of light or other electromagnetic radiation through the body of a filter (filter media) at least once, a photo receiver/sensor positioned to detect the transmitted electromagnetic radiation once it passes through the filter media, and a processor for receiving signals from the receiver/sensor and communicating a notice when the level of obscurant reaches a predetermined value.

One aspect of the present invention relates to optimization of the filter detector to function with very (optically) dense dust filters which are designed to remove relatively small particles (i.e., submicron sized). Particles of this size often agitate allergy sufferers. A second aspect of the invention relates to increased battery lifetime for battery operated dust filter detectors.

A clogged filter detector has a transmitter and a sensor which are preferably held in place by a transmitter bracket and a sensor bracket, respectively. The transmitter emits a beam of electromagnetic radiation, and the sensor is positioned in the path of this beam at a point such that the beam travels through a filter between the transmitter and the sensor. The transmitter and sensor are preferably mis-aligned with the air flow at the point where the beam contacts the filter. The transmitter alternates between a transmitting mode and a dormant mode, and the transmitter emits a plurality of electromagnetic pulses during each transmitting mode.

DETAILED DESCRIPTION

HVAC System

Figure 1:
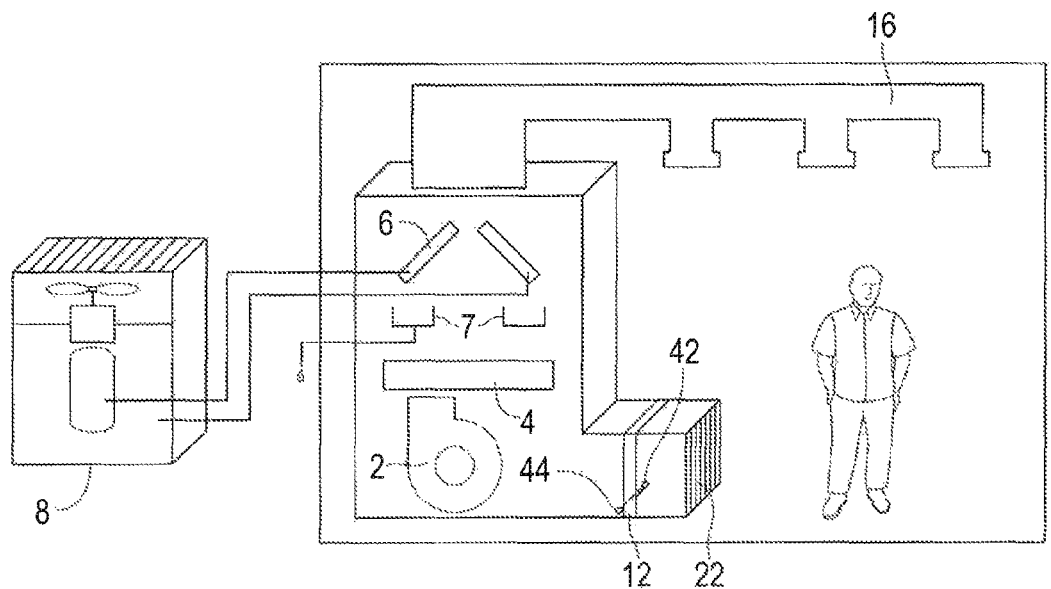
FIG. 1 is a diagram of a heating, ventilation, and air conditioning system.
Figure 2:
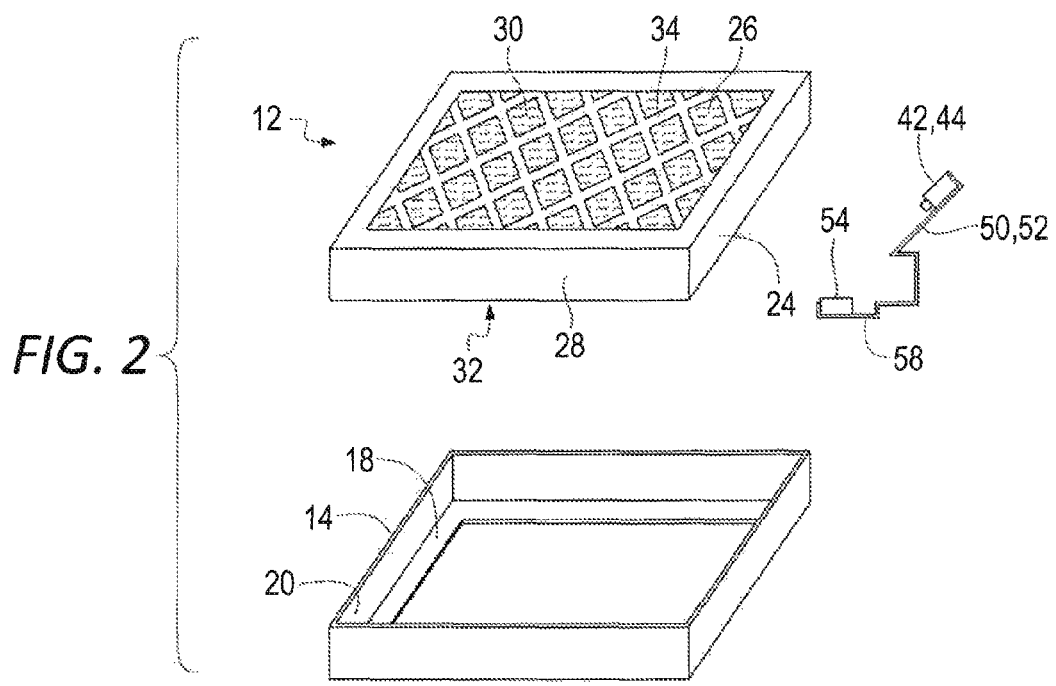
FIG. 2 is a diagram of a filter positioned over a filter receptacle, with a combined transmitter bracket, sensor bracket, and reflector bracket that fits onto the side of the filter, where the bracket is in position to be slide onto the filter before placing the filter in the filter receptacle.

A heating, ventilation, and air conditioning (HVAC) system 10 typically includes a filter 12 positioned in a filter receptacle 14, as seen in FIGS. 1 and 2. The filter 12 and associated filter receptacle 14 are often positioned in a duct 16 or plenum of an HVAC system 10. The HVAC system 10 typically includes a blower 2, a heating surface 4, cooling coils 6, a drain pan 7, a compressor 8, return and supply vents, a filter receptacle 14, ducts 16, and other components. The filter receptacle 14 is often positioned in a return line, and can include a filter receptacle ledge 18 that supports the filter 12 and prevents it from being drawn into the HVAC return ducts 14. The filter receptacle 14 also can include filter receptacle side plates 20, which can be perpendicular to the filter receptacle ledge 18. The filter receptacle side plates 20 are close to the edges of the filter 12, and help force returning air through the filter 12 instead of going around the filter 12. There can be a grill 22 positioned over the filter receptacle 14, where the air passes through the grill 22 before passing through the filter 12. The grill 22 can isolate and protect the filter 12 from a living area.

The filter 12 itself can have an external frame 24 that supports a filter body 26. The filter body 26 can be a mat, a flat sheet, a pleated sheet, a plurality of stacked sheets, or a wide variety of other shapes and configurations. The filter 12 has a filter edge 28, which is often the outer portion of the external frame 24, and the filter 12 also has a filter top surface 30 opposite a filter bottom surface 32. The filter body 26 can be held in place by the external frame 24, or by a filter support 34, or the filter body 26 may be self supporting. The filter support 34 can be a lattice system of paper, paperboard, metal, or other materials, or it can be netting or other materials positioned over, under, and/or around the filter body 26. The filter support 34 can help hold the filter body 26 together, or just add strength and durability to the filter 12 as a whole. The filter 12 is often a rectangular cube, in which case it has a filter edge 28 with four different surfaces and a filter top surface 30 opposite a filter bottom surface 32. However, other filter shapes are possible, such as discs, triangles, cylinders, or almost any shape.

During use, the HVAC system 10 forces air through the filter 12, and the air flow is typically perpendicular to the filter top surface 30 and the filter bottom surface 32. In other embodiments, air flow can impact a filter 12 at various angles, particularly if the filter receptacle 14 is close to a bend or corner in the duct 16. The air flow typically enters the filter body 26 from the filter top surface 30, and exits the filter body 26 from the filter bottom surface 32. Dust and other particulate matter gradually accumulates on the filter top surface 30 and throughout the filter body 26, and the accumulating dust slowly clogs the filter 12. The filter 12 resists air flow more and more as dust accumulates in the filter 12, and the accumulated dust actually serves to filter more dust from the returning air. Therefore, a dirty filter 12 may clog more rapidly than a clean filter 12, and the rate of clogging can increase over time.

Figure 3:
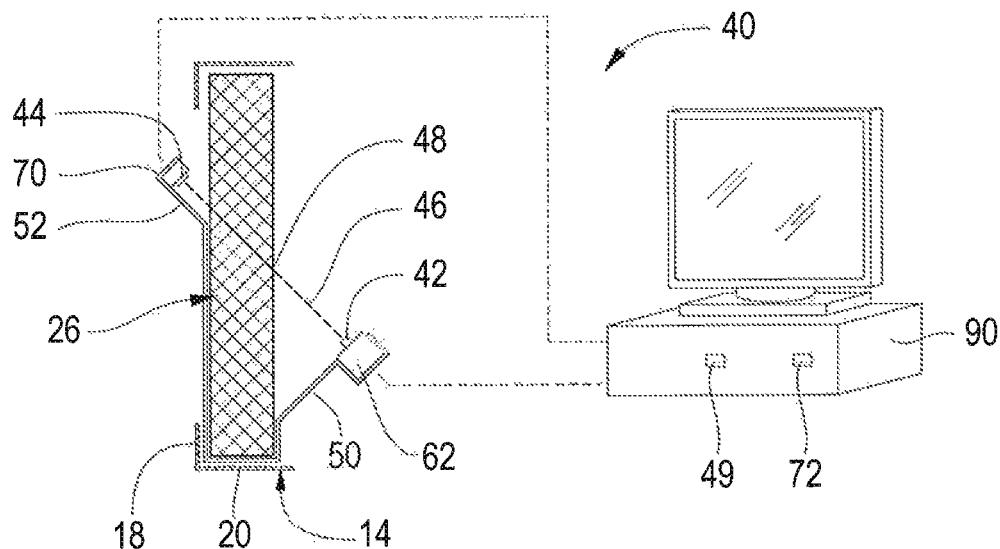
FIG. 3 is a diagram of one embodiment of a filter detector where the transmitter bracket and sensor bracket are connected to the filter receptacle.
Figure 4:
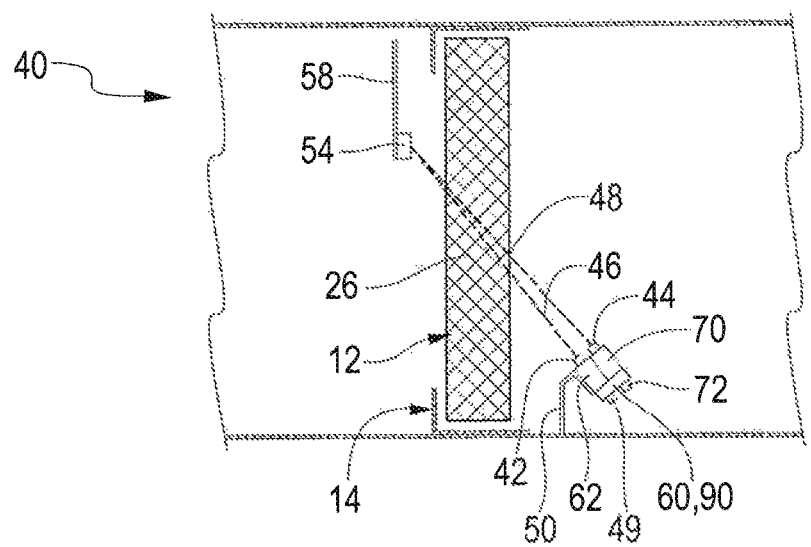
FIG. 4 is a diagram of a different embodiment of a filter detector where the transmitter and sensor brackets are one and the same, and are mounted on the wall of the duct. The reflector bracket is a different bracket which is also mounted on the duct wall.

The clogged filter detector 40 shown in FIGS. 3 and 4 and described herein can be used for HVAC systems 10, but it can also be used for many other applications. This includes filters 12 for paint spraying systems, ventilated electronic enclosures, clean rooms for dust sensitive manufacturing operations or other dust sensitive needs, and most other uses that requires filters to reduce the dust entrained in air or other gases. This description is primarily directed towards a HVAC system 10, but it should be understood that this is just one possible use of the clogged filter detector 40, and this description is intended to address systems other than HVAC systems 10, as will be understood by one skilled in the art.

Clogged Filter Detector and Transmitter

A filter detector 40 comprises a transmitter 42 and a sensor 44, as seen in FIGS. 3 and 4, with continuing reference to FIGS. 1 and 2. The transmitter 42 emits a beam 46 of electromagnetic radiation, such as infra-red light, near infra-red light, visible light, or other frequencies of electromagnetic radiation. The transmitter 42 will typically emit one frequency, or a limited range of frequencies, of electromagnetic radiation. The transmitter 42 can be a light emitting diode, a laser, or other sources of electromagnetic radiation.

The sensor 44 produces an electrical current when contacted by electromagnetic radiation, and the strength of the electrical current increases as the sensor 44 is contacted by more electromagnetic radiation. The sensor 44 can be a photo diode or a photo resistor, but other sensors known to those skilled in the art are also possible. The sensor 44 may be sensitive to a specific frequency or range of frequencies of electromagnetic radiation, so that the sensor 44 only generates an electrical current when contacted by certain frequencies or a certain range of frequencies of electromagnetic radiation. The response of the sensor 44, or the strength of the electrical current produced per quantity of received electromagnetic radiation, is also dependent on the frequency of the electromagnetic radiation.

Matching the frequencies of the transmitter 42 and the sensor 44 can improve the overall sensitivity of the filter detector 40. One frequency of electromagnetic radiation has a set wavelength, and preferably the peak wavelength at which the transmitter 42 emits electromagnetic radiation is within 200 nanometers of the peak sensitivity of the sensor 44, and more preferably the peak wavelength at which the transmitter 42 emits electromagnetic radiation is within 50 nanometers of the peak sensitivity of the sensor 44. In various embodiments, the peak transmitter frequency and the optimal sensor frequency are in the infra-red range, the near infra-red range, the visible light range, or other frequency ranges.

The transmitter 42 emits a beam 46 of electromagnetic radiation, and this beam 46 can be directed at the filter 12 such that the beam 46 strikes the filter 12 at a measurement point 48. The sensor 44 can be positioned so this beam 46 strikes the sensor 44 after the beam 46 strikes the measurement point 48 and passes through the filter 12. As dust and other particulates accumulate on the filter 12, the strength of the beam 46 which passes through the filter 12 and strikes the sensor 44 decreases, because the increasing accumulation of dust and other particulates increasingly block the beam 46. Therefore, the amount of dust accumulation on the filter 12 can be measured by recording the amount of electrical current produced by the sensor 44 when the filter 12 is clean, and comparing that to the amount of electrical current produced by the sensor 44 as the filter 12 gradually accumulates dust.

Figure 5:
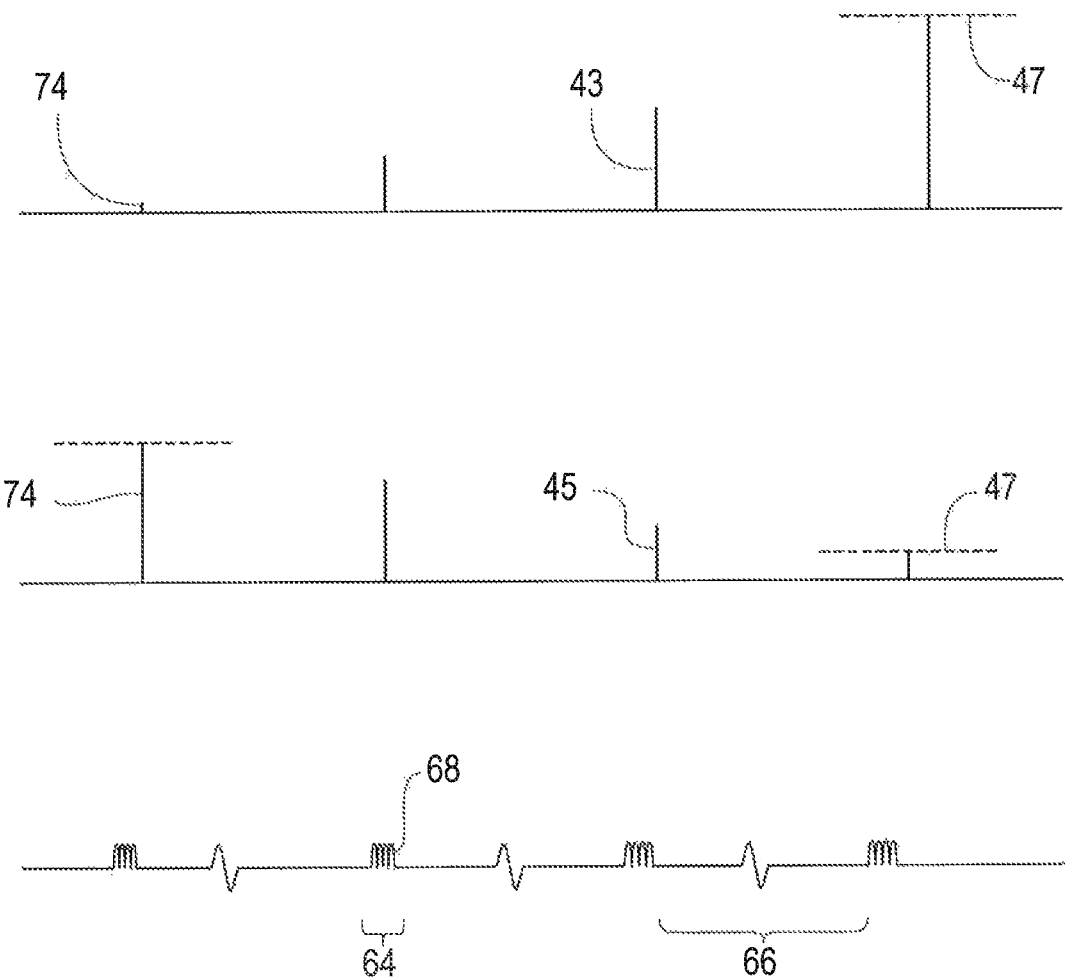
FIG. 5 is a series of graphs over time showing the strength of the transmitted electromagnetic radiation in the bottom graph, the sensor reading based on the transmitted electromagnetic radiation aligned with and over the bottom graph, and the calculated clogging level aligned with and over the sensor reading graph.

To simplify terminology, a "sensor reading" 45 is defined as a measurement of the amount of electrical current produced by the sensor 44, especially when the transmitter 42 is transmitting a beam 46 of electromagnetic radiation. A "clogging level" 43 is defined as a percentage based on the number 1 minus the ratio of the current sensor reading 45 divided by the sensor reading 45 when the filter 12 was new or freshly cleaned. One example of sensor readings 45 are shown in FIG. 5, with continuing reference to FIGS. 1-4.

There is no exact amount of dust that clogs a filter 12, but the filter detector 40 can use a set clogged level 47 as the clogging level 43 that defines when a filter 12 is clogged. Therefore, the set clogged level 47 is the percentage reduction of the sensor reading 45 over time that is used to notify the user when the filter 12 is clogged. The filter detector 40 can also include an alarm sensitivity adjustment 49 which can be used to adjust or change the set clogged level 47, and the alarm sensitivity adjustment 49 can be positioned in a wide variety of locations on the filter detector 40 so as to be convenient for the user. For example, the alarm sensitivity adjustment 49 (as well as any other operating controls) can be positioned with the transmitter 42, the sensor 44, on a bracket, or even remotely, such as with a remote computer or other related electronic device.

The transmitter 42 can be held in place by a transmitter bracket 50, and the sensor 44 can be held in place by a sensor bracket 52. The transmitter bracket 50 and the sensor bracket 52 can be connected to the filter receptacle 14 to hold them in place when the filter 12 is removed for cleaning or replacement. In other embodiments, the transmitter bracket 50 and/or the sensor bracket 52 can be connected to the filter 12 itself, the walls of the duct 16, the grill 22, or to any other structure that can secure the transmitter 42 and sensor 44 in the proper positions.

The transmitter and sensor brackets 50, 52 should hold the transmitter 42 and sensor 44 in a position that is mis-aligned with the air flow through the filter 12 at the measurement point 48, so that the transmitter 42 and sensor 44 do not block air flow at the measurement point 48. Air carries entrained dust to the filter 12, and this entrained dust gradually accumulates on the filter 12. The dust accumulation is measured at the measurement point 48, so air flow at the measurement point 48 should be representative of the entire filter 12. Dust accumulation is measured at this filter surface measurement point 48 and also within the filter body 26 along the optical path of the beam 46 between the transmitter 42 and sensor 44. Blocking air flow to the measurement point 48 would reduce the amount of dust accumulation at the measurement point 48. Therefore, aligning the sensor 44 or transmitter 42 with the air flow through the filter at the measurement point 48 could result in an inaccurate filter detector 40 because the filter detector 40 would not accurately measure the total dust accumulation on the largest part of the filter 12 where air flow is not obstructed.

If the air flow is perpendicular to the filter top surface 30, the transmitter 42 can be held at a position over the filter top surface 30 or adjacent to the filter top surface 30 with the beam 46 directed at an acute angle toward the filter top surface 30. This secures the transmitter 42 to the side of the air flow through the measurement point 48, so the air flow through the measurement point 48 is not obstructed. The sensor 44 can then be positioned in line with the beam 46 so the sensor 44 can also be positioned to the side of the air flow through the measurement point 48. The transmitter 42 and sensor 44 are then mis-aligned with the air flow through the filter 12 at the measurement point 48 because the transmitter 42 and sensor 44 are to the side of the air flow path through the measurement point 48 on the filter 12. There is frequently limited space in and around the filter receptacle 14 to mount the filter detector 40, so the transmitter 42 and sensor 44 may have to be close to the surface of the filter 12. This close positioning increases the importance of mis-aligning the transmitter 42 and sensor 44 with the air flow through the filter 12.

The sensor 44 should be positioned in the path of the beam 46 at a point after the beam 46 has passed through the filter 12. This can be accomplished in many ways. The transmitter bracket 50 and the sensor bracket 52 hold the transmitter 42 and the sensor 44 in position, so these brackets 50, 52 are used to position the transmitter 42 and sensor 44. In one embodiment, the sensor 44 is secured on the opposite side of the filter 12 as the transmitter 42. This can be done by either positioning the sensor 44 directly in line with the beam 48 emitted from the transmitter 42, or by positioning one or more reflectors 54 directly in line with the beam 48 emitted from the transmitter 42 such that the reflectors 54 direct the beam 48 to the sensor 44. Alternatively, the transmitter 42 and sensor 44 can be positioned on the same side of the filter 12, and a reflector 54 can be positioned on the opposite side of the filter 12 directly in line with the beam 48 emitted from the transmitter 42 such that the beam 48 is directed to the sensor 44. More than one reflector 54 can be used, if desired. The beam 48 has to pass through the filter 12 at least twice when the transmitter 42 and sensor 44 are on the same side of the filter 12, and this can reduce the overall signal strength reaching the sensor 42. Some filters 12 have an external frame 24 that limits access to the filter top or bottom surface 30, 32, so the transmitter bracket 50 and the sensor bracket 52 can be adjustable so the measurement point 48 can be moved as necessary.

In one embodiment, the reflector 54 can be a retroreflector, and the transmitter 42 and sensor 44 can be positioned very close to each other. In this embodiment, the transmitter bracket 50 and the sensor bracket 52 can be one and the same bracket. The transmitter 42 can be positioned within a housing, and in this embodiment it is possible for the transmitter 42 and the sensor 44 to be positioned in the same housing. The reflector 54 can be secured in place in many ways. Some techniques for securing the reflector 54 include a reflector bracket 58, or the reflector 54 can be secured to the filter receptacle 14, the internal walls of the duct 16, or even directly to the filter 12. Use of a retroreflector type reflector 54, which reflects electromagnetic radiation back to the source of that electromagnetic radiation, can simplify the positioning of the transmitter 42 and sensor 44 because they can be co-located.

The filter detector 40 preferably requires the transmitter 42 to emit a relatively consistent amount of electromagnetic radiation over time, so the change in the sensor reading 45 is based on accumulated dust on the filter 12 and not on a change in the performance of the transmitter 42. One or more batteries 60 can be used to power the transmitter 42, and they may also be used for operation of the sensor 44 and other components of the filter detector 40 requiring electrical power. If the battery 60 loses power over time, the beam 46 emitted from the transmitter will decrease in strength, and this will indicate the filter 12 is becoming clogged. That means a dying battery 60 will falsely indicate a clogged filter 12, instead of falsely indicating a clean filter 12, and this can call attention to the filter detector 40 for battery changing or charging. In some embodiments, the filter detector 40 will notify the user when the battery 60 loses voltage, such as with an audible sound, a light, or by other techniques. The filter detector 40 can also be powered by alternating current or direct current supplied from sources other than a battery 60, such as power provided by a utility company or from a generator.

The beam 46 can be polarized, and the sensor 44 can include a filter that reduces electromagnetic radiation that is not polarized the same as the beam 46 when the beam 46 reaches the sensor 44. This can reduce interference from outside sources of electromagnetic radiation, such as sunlight, light bulbs, or other sources. Also, the beam 46 can be focused to a narrow beam 46 to increase the amount of emitted electromagnetic radiation that can actually reach the sensor 42, but a more narrow beam 46 requires more accurate placement of the sensor 42 to ensure the sensor 42 is in line with the beam 46. A more narrow beam 46 may be beneficial for more optically dense filters 12, because the relatively stronger signal strength may be necessary to sufficiently penetrate the filter body 26.

In one embodiment, the transmitter 42 can have an aperture diameter of 5 mm. In other embodiments, the aperture diameter of the transmitter 42 can be approximately between 5 mm to 10 mm, but other ranges are also possible. In yet another embodiment, the transmitter 42 can be a laser diode.

Controller for the Transmitter

Figure 6:
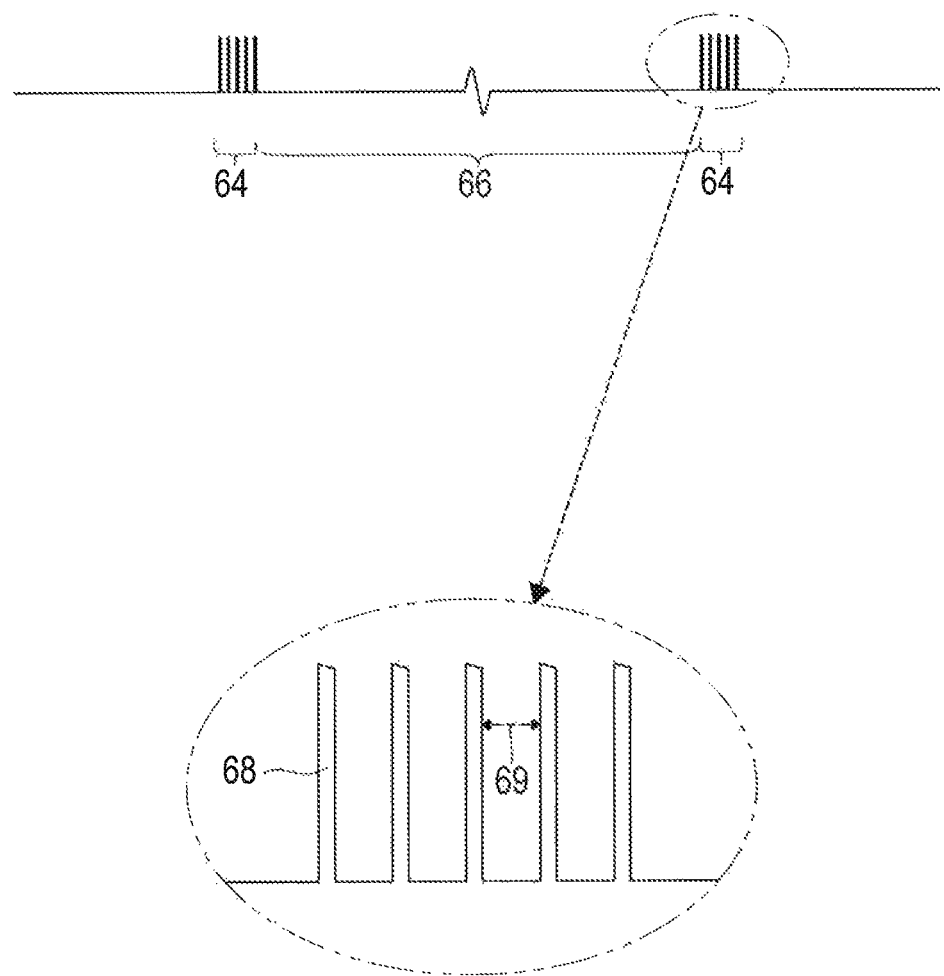
FIG. 6 is a graph over time showing the strength of the transmitted electromagnetic radiation from the transmitter.

A controller 62 can be used to control the operation of the transmitter 42. The controller 62 can be electrically connected to the transmitter 42, but it may also be possible for the controller 62 to utilize wireless technology, known to those of skill in the art, to control the transmitter 42. The controller 62 can direct the transmitter 42 to alternate between a transmitting mode 64 and a dormant mode 66, as seen in FIG. 6, with continuing reference to FIGS. 1-5. The transmitter 42 does not transmit significant amounts of electromagnetic radiation during the dormant mode 66. The transmitter 42 emits the beam 46 during the transmitting mode 64, and the transmitter uses far more power during the transmitting mode 64 than during the dormant mode 62. The filter detector 40 can save power, and thereby extend battery life if powered by a battery 60, by using lengthy dormant modes 66 separated by relatively short transmitting modes 64.

In one embodiment, the controller 62 can adjust and vary the length of the dormant mode 66 based on the sensor reading 45 during at least one previous transmitting mode 64. For example, the controller 62 can set the dormant mode 66 for 72 hours if the clogging level 43 indicates the filter 12 is less than 80% clogged, and the controller 62 can change the dormant mode 66 to 24 hours when the clogging level 43 indicates the filter 12 is at least 80% clogged, but not more than 90% clogged. The controller 62 can then change the dormant mode 66 to 6 hours when the clogging level 43 indicates the filter 12 is at least 90% clogged, and the set clogged level 47 may be at a clogging level 43 of 95%. The controller 62 can be set to change the length of the dormant mode 66 when the clogging level 43 reaches one or more preset values. The preset values can vary for many reasons, including different users or different applications, and the preset values can even be adjustable by the user, if desired. There can be any number of different dormant mode lengths based on the clogging level 43, and there can even be an algorithm to continuously adjust the length of the dormant mode 66 based on the clogging level 43, if desired.

A filter 12 tends to clog relatively slowly, so frequent tests are not necessary when the filter 12 is relatively clean. As the filter 12 becomes more clogged, the length of the dormant mode 66 can be shortened so there is not a significant delay between the time when the filter 12 becomes clogged and the time for the filter detector 40 to test the filter 12 for clogging. This can help insure a user is promptly notified when the filter 12 becomes clogged, but also helps save power when frequent testing is not necessary. Power saving can be particularly desirable when the filter detector 40 is battery 60 powered, because it can extend the battery life.

Changing the length of the dormant mode 66 can be based on one single sensor reading 45, but the trigger to change the dormant mode 66 can also be more than one consecutive sensor readings 45. Requiring more than one consecutive sensor reading 45 to change the length of the dormant mode 66 can help reduce changes based on a single errant reading. Other parameters can also be used to trigger changes in the length of the dormant mode 66, such as time and user inputs.

The controller 62 can direct the transmitter 42 to emit a plurality of electromagnetic radiation pulses 68 during a single transmitting mode 64, where the pulses 68 are separated by periods of inactivity (referred to as off-times 69) in the transmitting mode 64. Emitting pulses 68 can have several advantages for the transmitter 42. For example, the periods of off time 69 between pulses 68 can help minimize and control overheating, because the transmitter 42 does not generate heat during periods of off-time 69. The pulses 68 can also allow a battery 60 to regain voltage, because voltage from a battery 60 can decrease while the transmitter 42 is emitting a beam 46, and then recover during periods of off-time 69. Pulses 68 can also help reduce "noise" in the sensor reading 45, because the sensor 44 will have several different readings within one transmitting mode 64, and these different readings can be averaged. Background noise will tend to increase or decrease the sensor reading 45 for each individual pulse 68, but averaging the sensor readings 45 for several different pulses 68 tends to reduce the noise, because background noise that increases one reading is cancelled out by background noise that decreases a different reading. Background noise ban be further decreased by increasing the number of pulses 68 in a single transmitting mode 64.

In some embodiments, the transmitting mode 64 will be 1 second or less, and there can be 64 to 128 pulses 68 during the transmitting mode 64. The duty cycle during the transmitting mode can be about 50% or less, or even 10% or less in alternate embodiments, where the duty cycle is the ratio of the pulse 68 time to total time during the transmitting mode 64. The total time during the transmitting mode 64 is the sum of the time for the pulses 68 and the off-time 69. The length of the transmitting mode 64, the dormant mode 66, the number of pulses per transmitting mode 64, and the duty cycle during the transmitting mode 66 can all vary for different filters 12, filter uses, and other design and operation considerations.

Processor for the Sensor

A processor 70 can be used to control the sensor 44 and/or measure the sensor readings 45. Depending on the type and characteristics of the sensor 44 used, the processor 70 can direct the sensor 44 when to operate, and the processor 70 can measure the amount of electrical current generated by the sensor 44 and convert that measurement into the sensor reading 45. This can involve various techniques, such as but not limited to amplifying the electrical signal, and converting the electrical signal into a digital value. The processor 70 can be electrically connected to the sensor 44, but the processor 70 (or at least some components of the processor) may be wirelessly connected to the sensor 44. In some embodiments, the processor 70 can communicate with the controller 62, and the processor can limit operation and/or readings from the sensor 44 to periods when the transmitter 42 is emitting a beam 46. This can include limiting operations and/or readings of the sensor 44 to the time of the pulses 68 during the transmitting mode 64. In some embodiments, the processor 70 and the controller 62 are combined in a single housing, and can even use shared wiring, circuits, and other components.

The filter detector 40 can include a calibration switch 72. The calibration switch 72 can be activated when a filter 12 is cleaned or replaced, and this can initiate calibration of the filter detector 40. The filter detector 40 is calibrated by measuring the sensor reading 45 when the calibration switch 72 is activated, and that sensor reading 45 is saved as the calibration sensor reading 74. As time passes, the filter 12 becomes more clogged, and the sensor readings 45 become smaller because less electromagnetic radiation passes through the filter 12. The subsequent sensor readings 45 are compared to the calibration sensor reading 74 to determine the clogging level 43 of the filter 12. As the difference in the current sensor reading 45 and the saved calibration sensor reading 74 become larger, the clogging level 43 of the filter 12 increases, and the degree of clogging is associated with the clogging level 43 of the filter 12.

In some embodiments, the filter receptacle 14 is open to sunlight or other bright lights when the filter 12 is cleaned or replaced, and sunlight or other bright lights can disrupt the accuracy of a calibration sensor reading 74. In some embodiments, the filter detector 40 and the calibration switch 72 are only accessible when the filter receptacle 14 is open. Therefore, activation of the calibration switch 72 can activate the processor 70 and the controller 62 to test, measure, and record the calibration sensor reading 74 after a set calibration delay time interval has passed. This can give the user time to close the filter receptacle 14 and thereby block unwanted outside interferences during measurement of the calibration sensor reading 74. The filter 12 is still considered freshly washed, new, or freshly changed after the calibration delay time interval has passed, because the calibration delay time interval is small compared to the time necessary for the filter 12 to become clogged.

In some embodiments, there can be more than one calibration sensor readings 74. The processor 70 and/or controller 62 can record a calibration sensor reading 74 when the calibration switch 72 is activated, as well as recording one or more calibration sensor readings 74 after the calibration delay time interval. If more than one calibration sensor reading 74 is measured, the processor 70 or other components of the filter detector 40 can use different techniques to measure, determine, and save the calibration sensor reading 74 used for determining the clogging level 43. These different techniques include, but are not limited to: (i) the average of the various calibration sensor readings 74; (ii) the last of the calibration sensor readings 74; or (iii) when two or more calibration sensor reading measurements are within a set range of each other, the calibration sensor reading 74 can be the average of the sensor readings 45 that are within the set range of each other.

Computer

In some embodiments, the filter detector 40 can include a computer 90, or the filter detector 40 can communicate with a separate computer 90. The computer 90 can be integrated with the controller 62 and the processor 70, or it can be a separate unit, or there may not be a computer 90 at all. Some users have to maintain several different filters 12, and it can become challenging to keep track of all the different filters 12. The processor 70 can transmit sensor readings 45 or clogging levels 43 to a computer 90 to facilitate tracking of several different filters 12. There can be a plurality of processors 70 that transmit sensor readings 45 or clogging levels 43 to the computer 90, and the computer 90 can track the values for each different processor 70 and associated filter 12. The computer 90 can save the calibration sensor reading 74 and calculate the clogging level 43 in place of the processor 70, and the processor steps associated with the calibration sensor reading 74 and clogging level 43 calculations can be equally applicable to the computer 90. The controller 62, processor 70, and computer 90 are all electronic components, and they can share the same housing and even some circuits, memory, or other components, so these components can be difficult to distinguish.

A computer 90 can store and analyze large amounts of data, and this can aid in maintaining filters 12. For example, the computer 90 can: (a) track and graph clogging levels 43 for a filter 12; (b) record HVAC or other filter maintenance, and compare the maintenance history to other filters, manufacturer recommendations, or other factors; and (c) record changes in operation or settings for the filter detectors 40. A computer 90 can integrate filter maintenance and record keeping into a more complete maintenance record keeping system, and can be used to maintain records for insurance purposes. Detailed records can help control costs by allowing a user to select the most cost effective filter 12, or to compare clogging level 43 to energy associated with a particular filter 12 to determine the most cost effective maintenance practices. The processor 70, controller 62, and computer 90 can communicate wirelessly or by hardwire, and it is even possible to integrate the processor 70 and/or controller 62 and/or computer 90.

In some embodiments, the filter detector 40 or the computer 90 can send notices 92 to the user. The notices 92 can be sent when a filter 12 becomes clogged, or based on almost any other trigger point desirable. The processor 70 or computer 90 can determine a filter 12 is clogged when the clogging level 43 reaches a set clogged level 47, and in some embodiments the set clogged level 47 can be adjusted by the user with the alarm sensitivity adjustment 49. In some embodiments, a notice 92 will only be sent if there are a plurality of consecutive readings that reach a set clogged level 47. This can reduce false notices 92 based on a bug or other debris temporarily being in the path of the beam 46. If a set clogged level 47 is met in one reading, but the next reading shows a clogging level 43 below the set clogged level 47, the requirement for a notice 92 is reset to require two or more consecutive readings that reach the set clogged level 47.

The notice 92 can be simple, such as a light that flashes and/or an audible signal such as a beeping sound when the filter 12 becomes clogged. This simple notice 92 can be local to the filter detector 40, or remote, as desired. In other embodiments, the notice 92 to the user can be more complex. For example, the notice 92 can be a text message, an e-mail, a telephone call, a radio call, a page, or other types of communication that notifies the user that a filter 12 is clogged, or that recommended maintenance is due, or any other notice 92 that is desirable to the user. The notices 92 can include an indication or label identifying the filter 12 requiring attention (such as the filter 12 with a clogging level 45 that has reached the set clogged level 47), as well as other information such as the last time maintenance was performed, the type of filter 12 required, the time span the filter 12 has been in service, and recorded notes relating to tools or special considerations for a particular filter 12.

Figure 7:
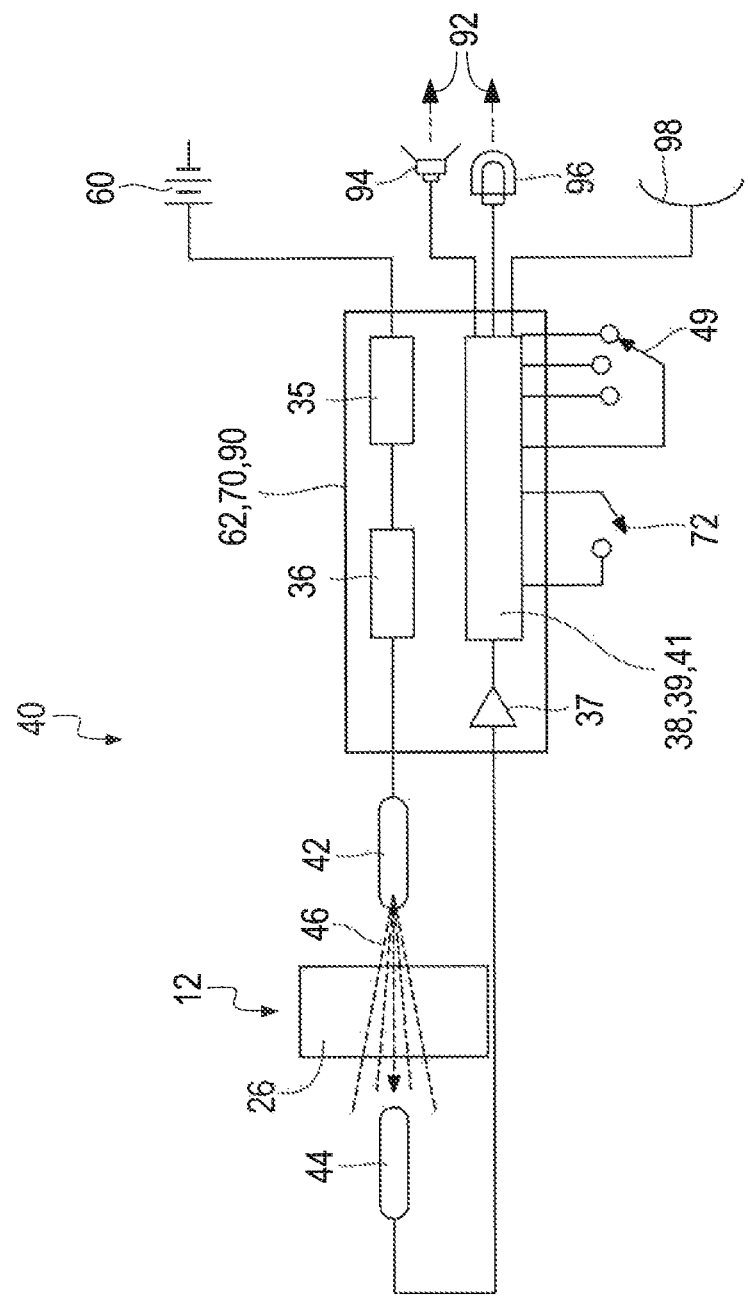
FIG. 7 is a schematic of one embodiment of portions of the filter detector.

One embodiment of the filter detector 40 is shown in FIG. 7, with continuing reference to FIGS. 1-6. This shows the controller 62, the processor 70, and the computer 90 located within the same housing, so the controller 62, processor 70, and/or computer 90 can be different parts of one electronics module. In this embodiment, the controller 62 comprises a voltage regulator 35 and a pulse generating switch 36, and the transmitter 42 is a light emitting diode (LED). The beam 46 passes through the filter 12 and strikes the sensor 44, which is a photo diode in this embodiment. The processor 70 comprises an amplifier 37, and a combined analog—digital converter 38, microprocessor controller 39, and digital storage chip 41 are also part of the processor 70 and/or the computer 90. This shows the calibration switch 72 and the alarm sensitivity adjustment 49, as well as a speaker 94, a light 96, and a radio transmitter 98 to send notices 92 to the user. Other embodiments are also possible.

EMBODIMENTS AND EXAMPLES

In one embodiment of the present invention, the transmitter 42 can be an infrared light emitting diode (LED). It is beneficial to match the frequencies of electromagnetic radiation emitted by the (LED) transmitters 42 with the sensor 44, which can be a silicon receiver. The frequency matching provides increased optical efficiencies over filter detectors 40 in which the peak transmitter frequency and the strongest sensor receiving frequency did not match, such as with an LED transmitter 42 which transmits in the red visible range and a sensor 44 with a peak receiving efficiency in the near infrared.

Figure 8:
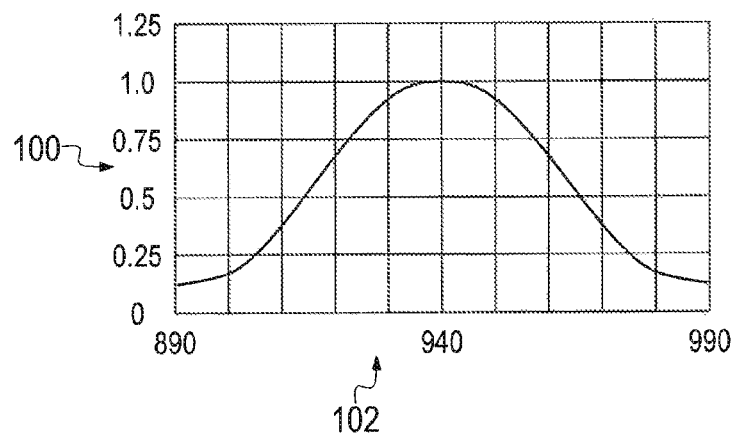
FIG. 8 is a graph of the output intensity of a transmitter compared to the wavelength of electromagnetic radiation being transmitted.
Figure 9:
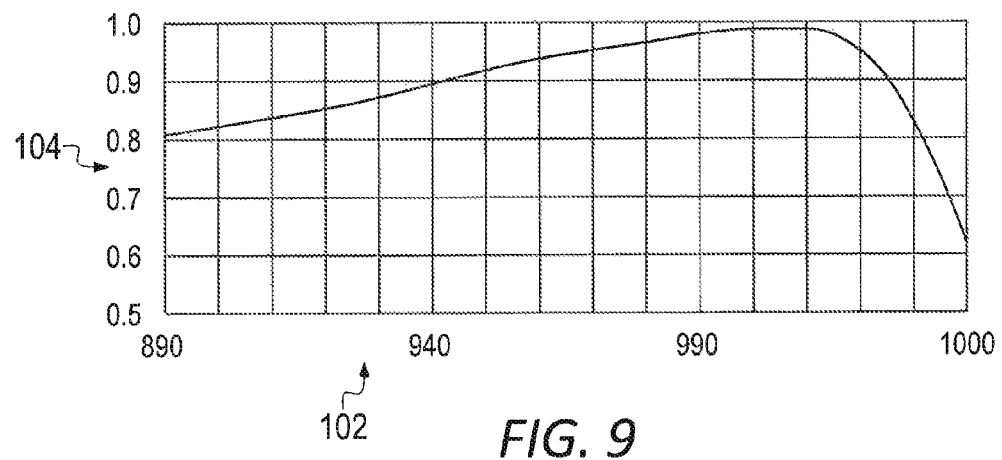
FIG. 9 is a graph of the relative sensor sensitivity compared to the wavelength of electromagnetic radiation received.

FIGS. 8 and 9 depict properties of one embodiment of an LED transmitter 42 and a photo-diode sensor 44, with continuing reference to FIGS. 1-7. The filter detector 40 works best when the peak relative LED transmitter output intensity 100 is a near match to the peak relative sensor sensitivity 104. The relative LED transmitter output intensity 100 is shown in FIG. 8, where the vertical axis of the graph depicts output intensity 100 in milliwatts per steradian (mW/SR), and the horizontal axis of the graph depicts wavelength 102 in nanometers (nm). The relative sensor sensitivity 104 is shown in FIG. 9, where the vertical axis depicts relative sensor sensitivity 104 and the horizontal axis depicts wavelength 102 in nanometers (nm). Many higher sensitivity and lower cost sensors 44 are most sensitive in the infrared range around a wavelength 102 of 940 nm, so the selection of an infrared transmitter 42 with a maximum output intensity 100 at approximately the same wavelength 102 can increase the efficiency of the filter detector 40.

Another aspect of the present invention relates to sensitivity improvements involving transmitted beam width (i.e., beam dispersion) and sensor field-of-view. For a point source, the transmitted beam width between half power points is approximately V/D, where X is the electromagnetic radiation wavelength and D is the aperture (diameter) of the transmitter output optic. The transmitter output optic is often a reflective parabolic or spherical surface, or a lens. In one embodiment, the aperture diameter of the transmitter is 5 mm. To take advantage of a relatively tight transmitted beam 46 (low beam dispersion), the transmitter 42 aiming is preferably such that the center of the transmitted beam 46 does not continuously "dance" across (or beyond) the sensor 44. In one embodiment of the filter detector 40, the transmitted beam 46 has over double the output intensity (130 milliwatts per steradian [mW/SR] versus 60 mW/SR) of other transmitted beams 46 with a wider beam dispersion, and pointing has been tested to be stable within ~1/10 beam width. Additional gains are achievable with transmitters 42 having more narrow beams 46, or using a laser diode, provided adequate pointing is maintained.

Another embodiment of the present invention relates to the pulsed transmitter format with a low duty cycle that can be used to allow a) the transmitter LED to cool between pulses 68 and b) to provide time for the battery voltage to recover between pulses 68. Likewise, the sensor viewing may be synchronized to match the transmitter pulsing, which decreases background "noise" accumulated by the receiver.

Figure 10:
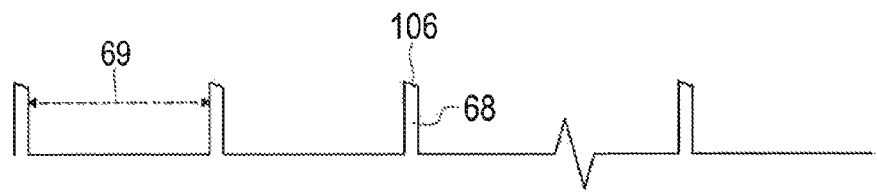
FIG. 10 is a graph of an electrical pulse train used to power a transmitter during a transmitting mode.

An electrical pulse train can be used to power a transmitter LED, where the transmitter 42 turns the electrical pulse train into pulses 68 of electromagnetic radiation, as shown in FIG. 10 with continuing reference to FIGS. 1-9. For simplicity, the electrical pulses 68 and the electromagnetic pulses 68 are given the same reference number 68 because they are directly related through the transmitter 42. The electrical off-times 69 between the pulses 68 during the transmitting mode 64 are also given the same name and reference number as the electromagnetic radiation off-times 69 between pulses 68 during the transmitting mode 64 for the same reason.

Each pulse 68 has a peak voltage 106 which is reached shortly after turn-on. From the peak voltage 106, the voltage sags until the electrical power is turned off at the end of the pulse 68, and this sag is shown by a downward sloped line extending to the right of the peak voltage 106 up to the point where the power is turned off at the end of the pulse 68. A significant off-time 69 allows the battery voltage to recover, (and the transmitter 42 to cool), provided the off-time 69 is long relative to the pulses 68. The ratio of the pulse 68 to the total transmitting mode 64 is called the duty cycle. A 10% duty cycle is typically adequate for battery voltage recovery.

Also, as discussed above, the averaging of the sensor readings 45 during each pulse 68 provides an improved signal-to-noise ratio. Therefore, a properly designed pulsed LED transmitter 42 and synchronized sensor 44 offers three advantages: (1) batter voltage recovery between pulses 68, (2) Transmitter LED cooling between pulses 68, and (3) improved signal to noise ratios from averaging sensor readings 45 from multiple pulses 68. With a 1 millisecond pulse length and a 10% duty cycle, one LED tested by the Applicant accepted up to 0.5 amp current pulses 68. A pulse length of about 1 millisecond used with this tested LED transmitter 42 and a photo-diode sensor 44 also provided adequate time for a relatively low power consuming, relatively low speed (low frequency response) analog-digital converter 38 to acquire and process the sensor reading 45.

Another aspect of the filter detector 40 relates to improved battery lifetime by utilizing variable dormant modes 66 between the active transmitting modes 64. For example, if it is determined that the transmitting modes 64 for filter tests should occur every 12 hours when the filter 12 nears a clogged condition, at the beginning of the measurement sequence (i.e., shortly after the filter 12 has been installed), the dormant mode 66 can be set at some higher threshold, for example, 48 hours. As the filter 12 soils and the (filter) penetrating electromagnetic radiation decreases, test intervals (and the associated dormant modes 66) are decreased until the measured electromagnetic radiation reaches the user preselected set clogged level 47 and the notice 92 is transmitted, which can be activation of a local and/or remote alarm.

While the invention has been described with respect to a limited number of embodiments, those skilled in the art, having benefit of this disclosure, will appreciate that other embodiments can be devised which do not depart from the scope of the invention as disclosed here. Accordingly, the scope of the invention should be limited only by the attached claims.

The invention claimed is:

1. A clogged filter detector comprising:
   a. a transmitter that emits a pulse of electromagnetic radiation;
   b. a receiver sensor;
   c. a transmitter bracket connected to the transmitter, where the transmitter bracket secures the transmitter such that the pulse of electromagnetic radiation contacts a filter at a measurement point, and where the transmitter bracket secures the transmitter in a position that is mis-aligned with an air flow through the filter at the measurement point;
   d. a sensor bracket connected to the sensor, where the sensor bracket secures the sensor in a position that is mis-aligned with the air flow through the filter at the measurement point, and where the sensor bracket secures the sensor in the path of the transmitted pulse of electromagnetic radiation in a position such that the transmitted pulse of electromagnetic radiation passes through the filter between the transmitter and the sensor;
   e. a controller that controls the transmitter such that the transmitter is alternatively in a transmitting mode having an associated transmitting mode time period or a dormant mode, and where the transmitter emits a predefined number of multiple pulses of electromagnetic radiation during each transmitting mode time period;
   f. a non-transitory tangible media containing software or firmware encoded thereon for operation by one or more processors, wherein the one or more processors reduce the impact of background noise reflected in sensor readings by determining an average sensor reading value for the transmitting mode time period based on the sensor readings associated with the predefined number of multiple pulses within the transmitting mode time period; and
   wherein the dormant mode is of a variable length and wherein the controller shortens the time between variable length dormant modes based at least in part on instruction from one or more processors that the filter is nearing a clogging level.

2. The filter detector of claim 1 where the total periods of inactivity between pulses during the transmitting mode are at least five times greater than the total time the transmitter emits a pulse of electromagnetic radiation during the transmitting mode.

3. The filter detector of claim 1 wherein the one or more processors and the controller are connected such that the sensor is activated when the transmitter is transmitting a pulse of electromagnetic radiation.

4. The filter detector of claim 1 further comprising:
   g. a calibration switch connected to the one or more processors, where the processors calibrate the filter detector at a set calibration delay time interval after the calibration switch is activated by measuring a calibration sensor reading, and where clogging level of the filter is determined by comparing the sensor reading during the transmitting mode time period to the calibration sensor reading; and
   wherein the filter detector transmits a notice when the measured clogging level reaches a set clogged level for two or more consecutive clogging level measurements.

5. The filter detector of claim 1 where the transmitter is powered by a battery.

6. A clogged filter detector comprising:
   a. a transmitter that emits a beam of electromagnetic radiation;
   b. a sensor;
   c. a controller that controls the transmitter such that the transmitter is alternatively in either a transmitting mode having an associated transmitting mode time period or a dormant mode, and where the transmitter emits a predefined number of multiple beams of electromagnetic radiation during each transmitting mode time period;
   d. a non-transitory tangible media containing software or firmware encoded thereon for operation by the one or more processors, wherein the one or more processors determine the average sensor reading value for the transmitting mode time period based on the sensor readings associated with the predefined number of multiple beams within the transmitting mode time period; and wherein the dormant mode is of a variable length and wherein the controller shortens the time between variable length dormant modes based at least in part on instruction from one or more processors that the filter is nearing a clogging level.

7. The clogged filter detector of claim 6 further comprising:
e. a transmitter bracket connected to the transmitter, where the transmitter bracket secures the transmitter such that the beam of electromagnetic radiation contacts a filter at a measurement point, and where the transmitter bracket secures the transmitter in a position that is mis-aligned with an air flow through the filter at the measurement point;
f. a sensor bracket connected to the sensor, where the sensor bracket secures the sensor in a position that is mis-aligned with the air flow through the filter at the measurement point, and where the sensor bracket secures the sensor in the path of the transmitted beam of electromagnetic radiation in a position such that the transmitted beam of electromagnetic radiation passes through the filter between the transmitter and the sensor.

8. The clogged filter detector of claim 6 further comprising a notice, where the filter detector transmits the notice when the clogging level reaches a set clogged level for two or more consecutive clogging level measurements.

9. The clogged filter detector of claim 8 where the notice is at least one of a text message, an e-mail, or a telephone call.

10. The clogged filter detector of claim 6 where a peak wavelength at which the transmitter emits electromagnetic radiation is within 50 nanometers of a peak sensitivity of the sensor.

11. The clogged filter detector of claim 6 wherein the determination of whether the filter is nearing a clogging level is based at least in part on the average sensor reading value from the transmitting mode time period.

12. A clogged filter detector comprising:
a. a transmitter that is alternatively in a transmitting mode or a dormant mode, wherein the transmitter emits a predefined number of multiple pulses of electromagnetic radiation when in the transmitting mode during a transmitting mode time period;
b. a sensor that produces an electrical current when contacted by a pulse of electromagnetic radiation, and where a sensor reading is based on the electrical current produced;
c. a transmitter bracket connected to the transmitter;
d. a sensor bracket connected to the sensor;
e. a non-transitory tangible media containing software or firmware encoded thereon for operation by the one or more processors, wherein the one or more processors determine a sensor reading value for the transmitting mode time period based on the sensor readings associated with the pulses within the transmitting mode time period, and wherein the determination of whether the filter is nearing a clogging level is based at least in part on the sensor reading value from the transmitting mode time period; and wherein the dormant mode is of a variable length and the time period between variable length dormant modes based at least in part on whether the filter is nearing a clogging level.

13. The clogged filter detector of claim 12 further comprising:
f. a transmitter bracket connected to the transmitter, where the transmitter bracket secures the transmitter such that the beam of electromagnetic radiation contacts a filter at a measurement point, and where the transmitter bracket secures the transmitter in a position that is mis-aligned with an air flow through the filter at the measurement point;
g. a sensor bracket connected to the sensor, where the sensor bracket secures the sensor in a position that is mis-aligned with the air flow through the filter at the measurement point, and where the sensor bracket secures the sensor in the path of the transmitted beam of electromagnetic radiation in a position such that the transmitted beam of electromagnetic radiation passes through the filter between the transmitter and the sensor.

14. The clogged filter detector of claim 13 further comprising:
h. a calibration switch connected to at least one other component of the filter detector, where the one or more processors measure a calibration sensor reading at a set calibration delay time interval after the calibration switch is activated, and where a clogging level is determined by comparing the sensor reading during the transmitting mode time period to the calibration sensor reading.

15. The clogged filter detector of claim 14 further comprising:
i. a computer, where the one or more processors transmit the clogging level to the computer; and
wherein the computer transmits a notice when the clogging level reaches a set clogged level.

16. The clogged filter detector of claim 12 wherein the sensor and the transmitter are located in separate housings.

17. The clogged filter detector of claim 12 where a notice to the user is at least one of a text message, an e-mail message, a telephone call, a radio transmittance, and a page.

18. The clogged filter detector of claim 17 where the notice is transmitted if the clogging level reaches the set clogged level for two or more consecutive clogging level calculations.

\* \* \* \* \*